United States Patent [19]

Schwartz

[11] 4,155,163
[45] May 22, 1979

[54] RELATOR ASSEMBLY

[76] Inventor: Robert Schwartz, 1271 Westfield Ave., Rahway, N.J. 07065

[21] Appl. No.: 819,864

[22] Filed: Jul. 28, 1977

Related U.S. Application Data

[63] Continuation-in-part of Ser. No. 759,020, Jan. 13, 1977, abandoned.

[51] Int. Cl.² .............................................. A61C 11/00
[52] U.S. Cl. ...................................................... 32/32
[58] Field of Search ............................................ 32/32

[56] References Cited
U.S. PATENT DOCUMENTS

| | | | |
|---|---|---|---|
| 2,334,643 | 11/1943 | Moore | 32/32 |
| 2,448,085 | 8/1948 | Dickson | 32/32 |
| 3,423,834 | 1/1969 | Irish | 32/32 |
| 3,465,443 | 9/1969 | Schwartz et al. | 32/32 |
| 3,693,260 | 9/1972 | Hernandez | 32/32 |
| 3,694,919 | 10/1972 | Lee et al. | 32/32 |
| 3,708,882 | 1/1973 | Guichet | 32/32 |
| 3,815,242 | 6/1974 | Martfay et al. | 32/32 |
| 3,930,312 | 1/1976 | Daub | 32/32 |
| 3,938,252 | 2/1976 | Polanco | 32/32 |
| 3,965,576 | 6/1976 | Eveland | 32/32 |

Primary Examiner—Robert Peshock
Assistant Examiner—Michael J. Foycik, Jr.

[57] ABSTRACT

Dentures or denture elements that are anatomically related to Camper's Plane are prepared employing the relator assembly of the present invention. The relator assembly is composed of (i) a vertically disposed support that is maintained in position with a stand member; (ii) a horizontally disposed occlusal base member; (iii) a maxillary base member that is pivotably connected to the upper portion of the support, the lower surface of the maxillary base member positioned in substantial vertical alignment with and in a plane parallel to the upper surface of the occlusal base member; (iv) cast positioning element located on the lower surface of the maxillary base member; (v) a labial drape locator that is adapted to be positioned on and removed from the upper surface of the occlusal base member; and (vi) an arch locator that is adapted to be positioned on and removed from the arch locator holder element of the labial drape locator.

4 Claims, 11 Drawing Figures

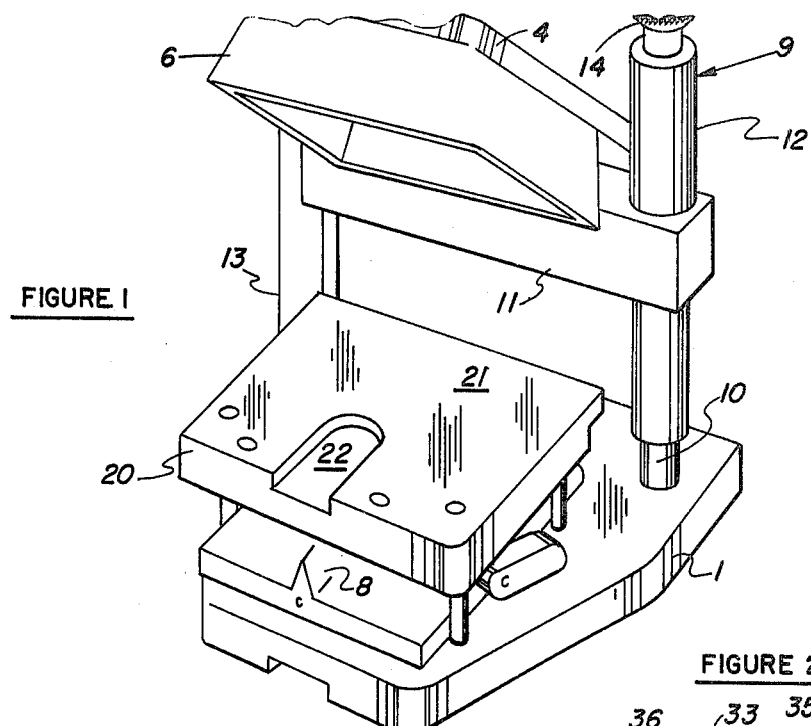
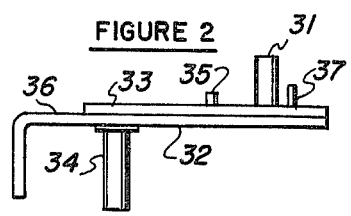
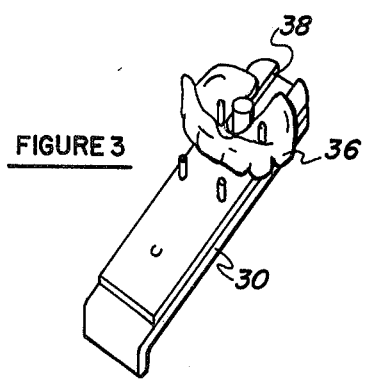
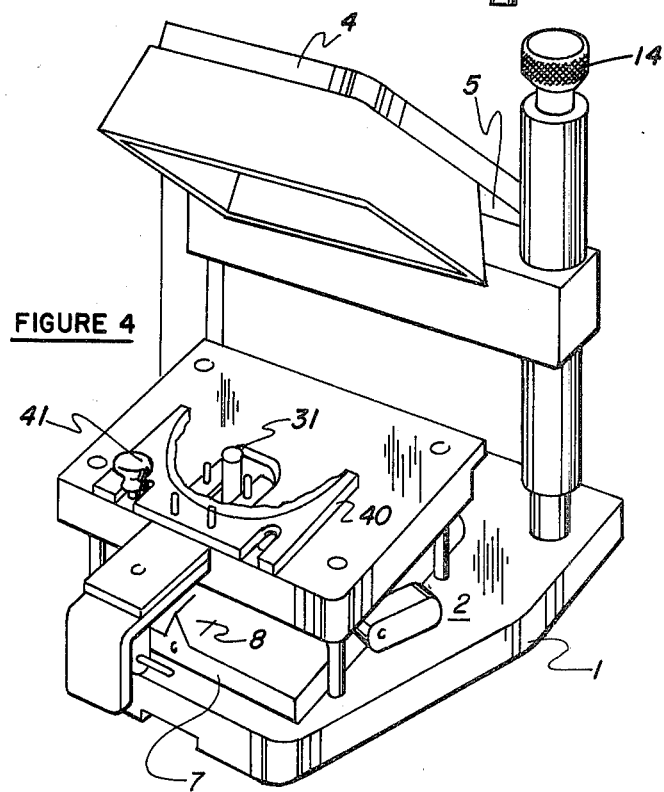

RELATOR ASSEMBLY

CROSS REFERENCE TO RELATED APPLICATION

This application is a continuation-in-part of Ser. No. 759,020, filed Jan. 13, 1977 and now abandoned.

BACKGROUND OF THE INVENTION

1. Field of the Invention

This invention is directed to a relator assembly useful for preparing dentures or denture elements that are anatomically related to Camper's Plane. More particularly, the invention is concerned with a mechanical assembly that can be employed to prepare dentures from prefabricated arch structures, arch elements or individual artificial teeth, which dentures are anatomically related to Camper's Plane.

2. Description of the Prior Art

Dental practitioners have used a wide variety of mechanical systems to prepare dental casts and finished dentures that are oriented to the horizontal, transverse and mid-sagital planes of the human skull. Examples of such devices are disclosed in U.S. Pat. No. 3,018,551 and U.S. Pat. No. 2,003,727.

The relator assembly of the present invention is a variant of the orthopedic relator assembly described in U.S. Pat. No. 3,465,443, issued Sept. 9, 1969, the disclosures of which are herein incorporated by reference. The device depicted in U.S. Pat. No. 3,465,443 is used to form standardized diagnostic dental casts having bases that are parallel to the dental plane of occlusion whereas the present relator assembly is adapted for the preparation of dentures or denture elements from dental casts whose bases are parallel to the dental plane of occlusion. Casts prepared as described in U.S. Pat. No. 3,465,443 are particularly suited for use with the device of the present invention.

SUMMARY OF THE INVENTION

In accordance with the present invention, dentures or denture elements that are anatomically related to Camper's Plane, that is, the plane defined by the hamular notches and the anterior palatine papilla of the maxillary dentition (also sometimes referred to as the hamular-incise plane) can be prepared readily from prefabricated dentures, denture elements or individual teeth, utilizing the relator assembly of the present invention. The relator assembly consists of five principal interconnected elements, namely, (i) a vertically disposed support means whose upper and lower ends are preferably vertically movable in relation to each other, (ii) a horizontally disposed occlusal base member, (iii) a maxillary base member, (iv) a labial drape locator and (v) an arch locator. The maxillary base member is connected to the vertically disposed support means and the lower surface of the maxillary base member is adapted to be placed in a position in substantial vertical alignment with and parallel to the upper surface of the occlusal base member. The lower surface of the maxillary base member is provided with cast positioning means. On the upper surface of the occlusal base member is located a removable labial drape locator and an arch locator. The labial drape locator comprises a removable pin member, and an elongated pin holder that serves to locate the pin member in a substantially vertical position, the inner and outer ends of the pin holder being horizontally adjustable relative to each other, and an arch locator holder. The arch locator element or elements positioned on the arch locator holder.

BRIEF DESCRIPTION OF THE DRAWINGS

The invention will be more readily understood by reference to the accompanying drawings in which:

FIG. 1 is a front elevational view of the relator assembly in which the maxillary base member is shown in a raised or open position;

FIG. 2 is a side view of the labial drape locator;

FIG. 3 is a top view of the labial drape locator;

FIG. 4 is a front elevational view of the relator assembly with the labial drape locator and one type of arch locator positioned in place on the upper surface of the occlusal base member;

Figure 9:
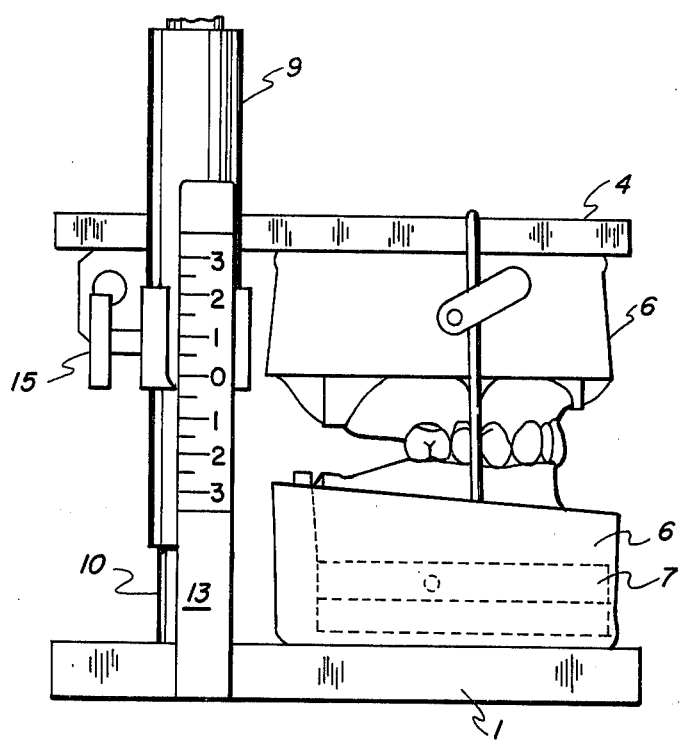
FIG. 9 is a side view of the relator with a maxillary cast and mandibular bite block in place.

Referring now to the drawings, reference number 1 represents the stand member or alternatively, a mandibular base member having an upper surface 2 and a lower surface 3. Reference numeral 4 refers to the maxillary base member of the relator assembly. Maxillary base member 4 has an upper surface and a lower surface 5. To the lower surface 5 of the maxillary base member 5 is connected cast positioning means 7, preferably enclosed with a flask-type structure that can be removed from maxillary base member 4 and employed in the further manufacture of the finished denture materials. In a preferred embodiment of the present invention, the upper surface of the stand member or mandibular base member 1 is also provided with cast positioning means 7. Cast positioning means 7 is composed of a blade structure 8 that extends longitudinally along the upper surface of the mandibular base member 2. A hole is bored through the blade structure at a location near the mid-point of the blade. The hole is adapted to receive a pin member 9. The pin is inserted into the hole of the blade member 8 during the formation of the cast used in the preparation of dentures and affords a means of rigidly positioning the finished cast onto blade structure 8. The preferred maxillary and mandibular cast positioning means are described and depicted in more detail in U.S. Pat. No. 3,465,443. A cast positioning means similar to that depicted on the mandibular base member 1 is also preferably located on the lower surface of the maxillary base member 4 within the flask structure 6. Locating the preferred cast positioning means within a flask 6 is shown in FIG. 9 (cast positioning means within the mandibular flask located on the upper surface 2 of the mandibular base).

The maxillary base member 4 is maintained in position above the upper surface of the stand or mandibular base member 1 by means of a vertically disposed, telescoping support means 9. Column 10 forms the lowermost portion of support means 9. The maxillary base member 4 is connected to cross bar 11 that is integrally attached to sleeve 12. Sleeve 12 slidably engages column 10. The outer terminal portion of crossbar 11 is bifurcated and adapted to slide over the outer surfaces of post 13 (see FIGS. 7, 9 and 11). Column 10 and post 13 are rigidly affixed to a stand member or to the preferred mandibular base member 1 depicted in the Figures. Preferably, the maxillary base member 4 is pivotably mounted on crossbar 11 using means not shown. The maxillary base member 4 is arranged on the support structure 9 in such a manner that the lower surface of the maxillary base member 4 can be positioned in substantial vertical alignment with and in a plane substantially parallel to the upper surface 21 of the occlusal base member 20. It is preferred that support member 9 be provided with means permitting the maxillary base member 4 to be moved vertically to and away from the upper surface 21 of occlusal base member 20. Vertical movement of the maxillary base member 4 is conveniently obtained by providing column 10 with an internally threaded axial bore and providing sleeve 14 with an adjusting screw arrangement that is adapted to engage the threaded surface of the internal axial bore contained within column 10. Adjusting screw 14 is maintained in position within sleeve 12 by means of a suitable bearing arrangement. The maxillary base member 4 can be locked into a given vertical location relative to the maxillary base member with set screw 15 which can be threaded against post 13. Set screw 15 is threaded through one element of the bifurcated terminal portion of crossbar 11.

Figure 6:
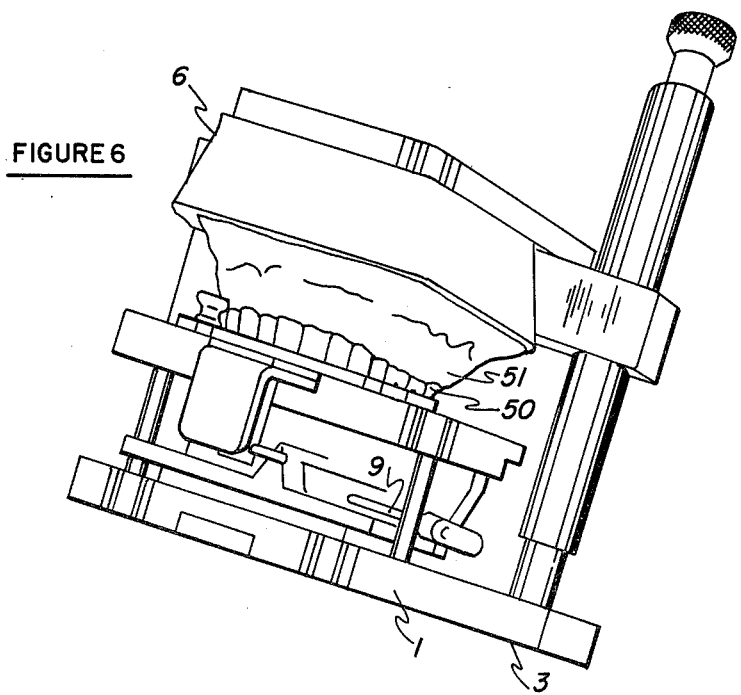
FIG. 6 is a front view of the relator assembly in use in the preparation of a full maxillary denture utilizing a prefabricated maxillary arch structure.
Figure 7:
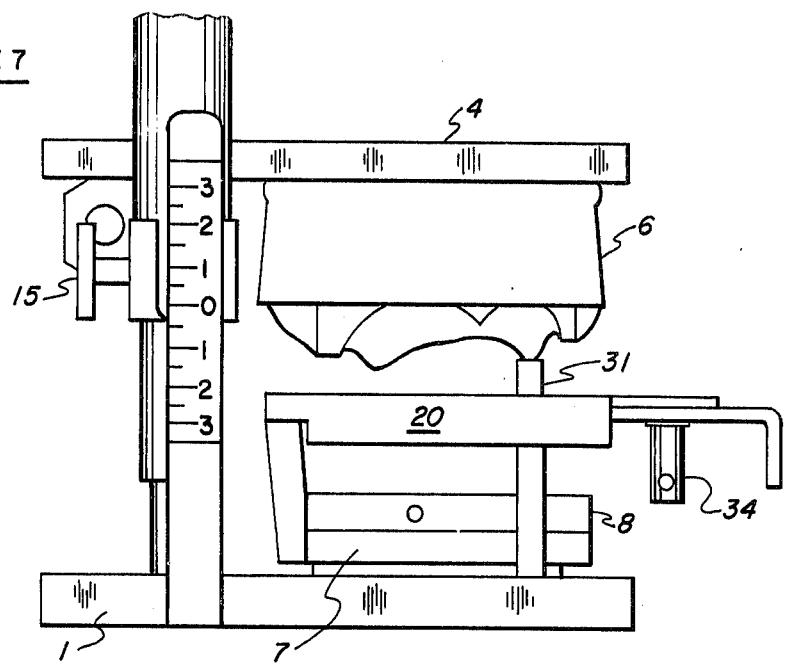
FIG. 7 is a side view of the relator assembly with the labial drape locator in place on the occlusal base and the pin member in contact with the palatine papilla of a maxillary cast.
Figure 11:
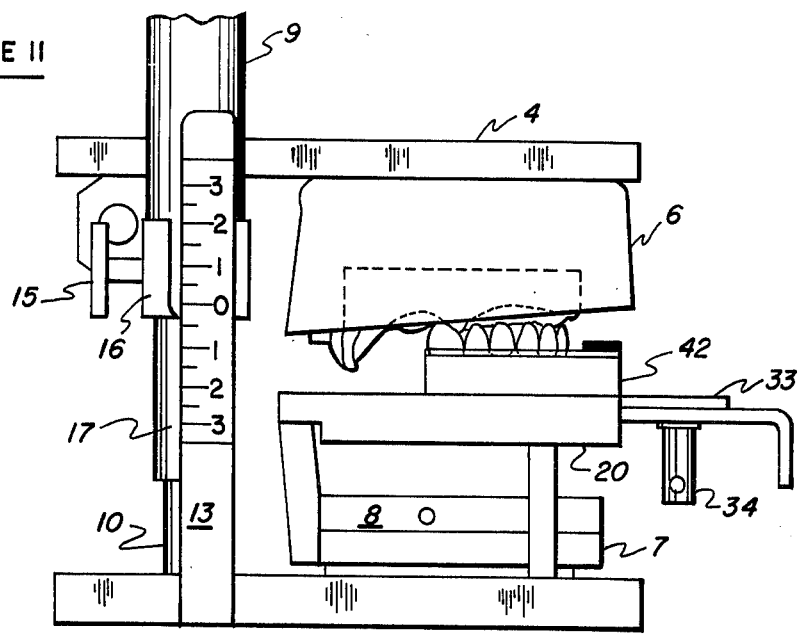
FIG. 11 is a side view of the relator assembly in use in the formation of a maxillary denture.

The occlusal base member 20 is adapted to be located above the stand member or mandibular base member 1. As noted before, the upper surface 21 of the occlusal base 20 is maintained in position in a plane parallel to the lower surface of maxillary base 4 when the maxillary base 4 is in a closed position (FIGS. 6, 7 and 11). Furthermore, the upper surface 21 is preferably also maintained in a plane parallel to the upper surface of mandibular base member 1. In one arrangement, the occlusal base 20 is located in position by means of legs that are located about the outer periphery of the lower surface of the occlusal base. The legs, in a preferred arrangement, rest on the upper surface of the mandibular base member 1. An alternate mode of supporting the occlusal base 20 in the desired position is shown in FIGS. 6, 7 and 11.

A notch or opening 22 of predetermined length and width is machined into the forward portion of the upper surface 21 of occlusal base member 20. Opening 22 is adapted to receive the inner end portion of the labial drape locator element 30 of the relator system (see FIGS. 2 and 3). The labial drape locator is adapted to be positioned on and removed from the upper surface of the occlusal base member 20. The labial drape locator comprises (i) a removable pin member 31, (ii) an elongated pin holder 32 that has an inner end and an outer end with the inner end adapted to locate and position pin member 31 in a plane substantially perpendicular to the upper surface 21 of the occlusal base member 20 and (iii) an arch locator holder 33. The arch locator holder 33 is interconnected to the pin holder 32 using a screw locking system 34. The arch locator holder 33 is horizontally adjustable relative to the inner end of said pin holder 32. Preferably, the upper surface of the arch locator holder 33 does not extend above the upper surface 21 of occlusal base member 20 (see FIG. 4) when the labial drape locator is placed within opening 22.

Figure 8:
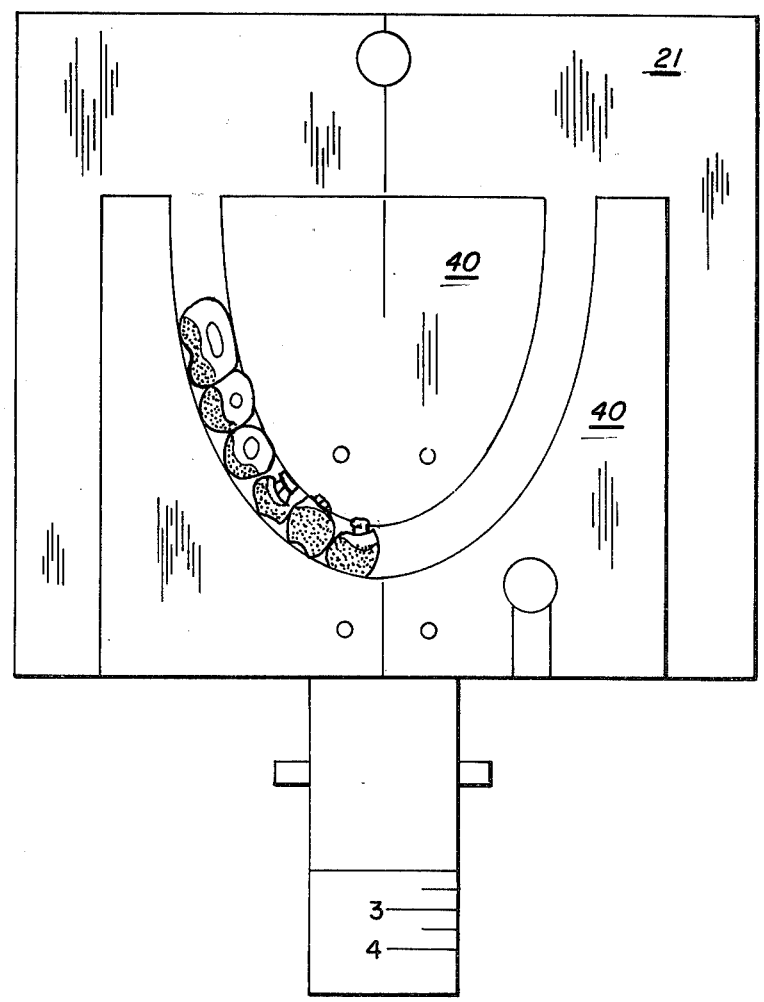
FIG. 8 is a top view of the occlusal base member with one type of arch locator positioned thereon.
Figure 10:
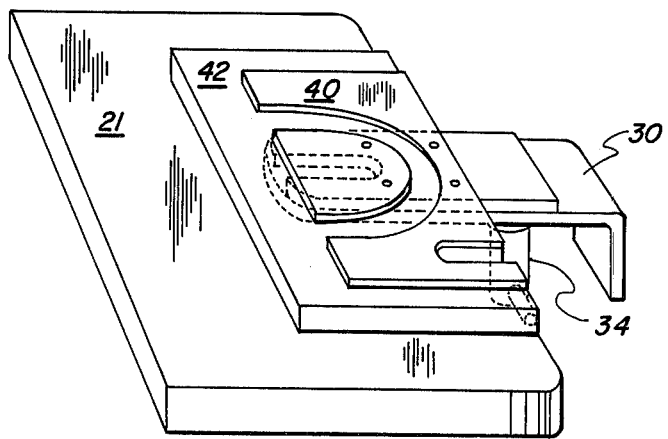
FIG. 10 is a side elevational view of the occlusal base member.

The final element of the relator assembly is arch locator 40. Arch locator 40 may be a single component (FIG. 4) or may be a multi-component configuration (FIG. 8). The arch locator 40 is adapted to be positioned on and removed from either arch locator holder 33 as in FIG. 4 or mandibular shim 42 as in FIGS. 10 and 11. As shown in FIG. 4, the arch locator 40 may be maintained in position on the upper surface 21 of occlusal base member 20 by means of studs 35 which are integrally connected to the upper surface of arch locator holder 33. Alternatively, as shown in FIG. 10, the elements of the arch locator may be positioned on studs located on the upper surface of the mandibular shim 42. The arch locator may be locked into position on the upper surface of occlusal base member 20 or mandibular shim 42 using a set screw 41. The arch locator 40 may be any suitable configuration. The device functions to position a prefabricated arch structure or portion of an arch structure or one or more individual teeth upon the upper surface of occlusal base member 20 when the maxillary denture is prepared and optionally, upon the upper surface of the mandibular shim 42 when the mandibular denture is constructed. Similarly, as will be described in more detail hereinafter, pin member 31 may be of any suitable length depending upon the patient's dental anatomy.

The primary use of the relator assembly is in the formation of dentures or denture elements that are anatomically related to Camper's Plane using prefabricated dental arches or dental arch elements (one or more individual teeth). The relator assembly is used in conjunction with standardized dental casts having bases that are parallel to the dental plane of occlusion of the patient and are specifically oriented to Camper's Plane. Such casts may be obtained using the device and procedures specified in U.S. Pat. No. 3,465,433.

To prepare a maxillary denture using the relator assembly of the present invention, it is first necessary to locate or mount a standardized maxillary cast whose base is parallel to the patient's dental plane of occlusion (most preferably prepared as per U.S. Pat. No. 3,465,433) within cast positioning means 6. The maxillary cast should be located within cast positioning means 6 in such a manner that the Camper's Plane of the cast is substantially parallel to the lower surface of the maxillary base member 4. Furthermore, the maxillary cast should be adjusted horizontally on the cast positioning means such that the palatine papilla of the cast is directly above pin member 31 when pin holder 32 of the labial drape locator 30 is fully inserted within opening 22.

The labial drape locator 30 is then employed to obtain a measurement of the proper incisal length and labial drape of the patient. This is accomplished by mounting a model 36 of the six anterior maxillary teeth of a selected arch size on studs 37 that are located on the upper surface of arch locator 33. The model 36 is fabricated to permit model 36 (and arch locator holder 33) to be moved to and away from pin 31. A pin 31 of from about 4 to 20 millimeters in length is then inserted within a hole formed in pin holder 32. The labial drape locator is placed within the patient's mouth with the top of pin member 31 resting against the palatine papilla of the patient. Thereafter, the dental practitioner obtains the proper aesthetic appearance of the model 36 within the patient's mouth by using a pin 31 of proper height in order to secure proper incisal length and/or by increasing or decreasing the horizontal distance between the pin member (which is positioned on the patient's palatine papilla) relative to the front portion of model 36 by making appropriate adjustments of pin holder 32 relative to arch locator holder 33. This latter adjustment is made to secure the proper aesthetic labial drape (upper lip placement relative to the outer surface of model 36). After the proper labial drape has been obtained, the pin holder and arch locator holder are locked into position relative to each other using screw member 34. The position of arch locator 33 relative to pin holder 32 may be recorded by reference to a scale superimposed upon the upper surface of pin holder 32.

Thereafter, maxillary base member 4 is brought into a closed position, that is, the lower surface of the maxillary base member is positioned in a plane parallel to the upper surface 21 of occlusal base 20. The model 36 is removed from studs 37 and the labial drape locator (adjusted as described above) is fully inserted within opening 22 and the maxillary base member is raised or lowered, as appropriate, using adjusting screw 14 until the uppermost surface of pin 31 makes contact with the palatine papilla of the cast located on the cast positioning means within flask 6 (see FIG. 7). The aforesaid operation serves to establish the proper distance of the cast relative to the upper surface 21 of the occlusal base member 20. The maxillary base member can be locked into place with set screw 15. The maxillary base member 4 is then pivoted away from the upper surface 21 of occlusal base member 20 (see FIG. 5), pin 31 removed from the labial drape locator without disturbing the position of the elements of the labial drape locator 30 within opening 22 and arch locator 40 locked into place over studs 35 of the labial drape locator 30 (see FIG. 4).

The arch locator may be of any suitable arch width depending upon the cross arch width distance of the patient being treated. Alternatively, an arch locator of variable arch width might be employed. Two different structures are suggested for use herein. The arch locator having the configuration shown in FIG. 4 is preferred for use in situations where a full prefabricated arch structure (see FIG. 5) is used in the preparation of the denture. The configuration depicted in FIGS. 8 and 10 is preferred when dentures are prepared from individual artifical teeth. The term "arch locator" as used herein is meant to include the arch shape structures as shown in FIG. 4, the two-element configurations of FIGS. 8 and 10 as well as other structures that will locate a prefabricated denture or denture element (one or more indivudal teeth) relative to one or more anatomical points (e.g., palatine papilla) of maxillary or mandibular casts affixed to maxillary base member 4.

Figure 5:
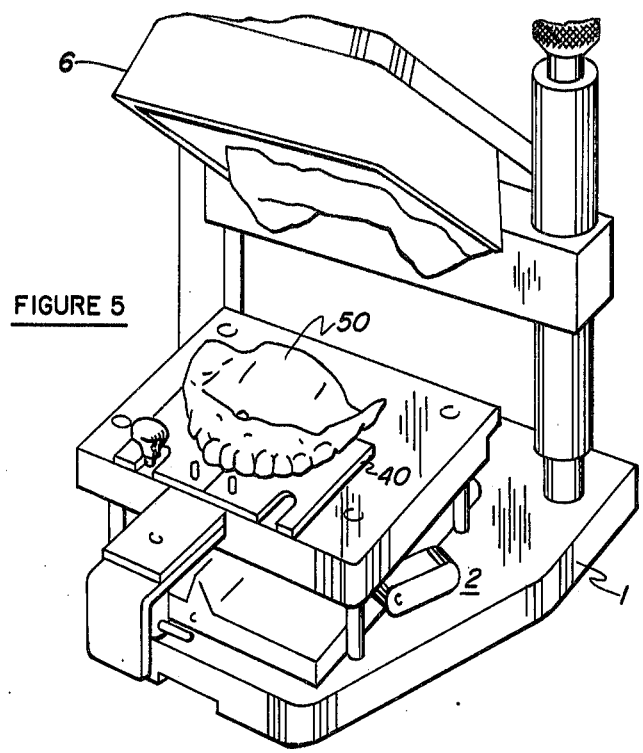
FIG. 5 is a front elevational view of the relator assembly of FIG. 4 with a prefabricated maxillary arch structure located within the arch locator and with a maxillary dental cast in place on the cast positioning means of the maxillary base member.

An appropriate prefabricated denture 50 is located within arch locator 40 (FIG. 5). The arch locator 40 serves to position the denture structure 50 on the occlusal base member 20 in a fixed position relative to the location of the palatine papilla of the maxillary cast contained within cast positioning means 6. The cast contained within cast positioning means 6 is then coated with a separating agent or lubricant, the prefabricated denture structure 50 filled with an impression material 51, and the maxillary base member again brought back into position such that the lower surface of the maxillary base member is parallel to the upper surface 21 of the occlusal base 20 (see FIG. 6). This series of steps serves to create an impression of the space between the maxillary cast and prefabricated denture.

To prepare a mandibular denture corresponding to the maxillary denture and utilizing a full prefabricated mandibular arch structure, the occlusal base 20 of the relator assembly is removed from its position on the upper surface 2 of the mandibular base 1. A completed mandibular cast of the patient's mouth, whose base is substantially parallel to the dental plane of occlusion of the patient is affixed to cast positioning means 7 that is located on the mandibular base 1. It is desirable that the base of the cast be maintained in position parallel to the upper surface of the mandibular base. The mandibular cast may be held in position by threading pin 9 through an appropriate hole in the cast and thence through backing means 8 of the cast positioning means 7. Thereafter, a prefabricated mandibular arch structure is placed upon the maxillary denture (prepared as described above) such that the dentition of the maxillary and mandibular prefabricated arch structures occlude in a manner sought by the practitioner. The prefabricated mandibular arch structure may be held in place on the maxillary denture with elastic bands whose ends are secured around studs that are positioned (not shown) on the upper surface of the maxillary base member.

The uncompleted structure, made up of the maxillary denture affixed to the maxillary cast located within cast positioning means 6 and the mandibular prefabricated arch structure attached thereto is moved away from the mandibular base by pivoting the maxillary base member to an open position. After the lower cast is coated with an appropriate separating material or lubricant, the mandibular cast is covered with an adequate quantity of an impression material of any suitable type. The aforesaid denture structure is then lowered into the fresh impression material making sure that the lower surface of the maxillary base member is again brought parallel to the upper surface of the mandibular base. Lowering the denture structure onto the fresh impression material, after making any necessary adjustments in the distance between the lower surface of the maxillary base member and the upper surface of the mandibular base member using adjusting screw 14 to accommodate the patient's anatomy, serves to prepare an impression of the space between the prefabricated mandibular arch structure and the mandibular cast positioned on the mandibular base member. After the impression material has been permitted to dry, the elastic bands used to hold the mandibular arch structure in place are trimmed away.

Dentures are fashioned from individual artifical teeth using the instant relator assembly. This is best accomplished using two-component arch relators as depicted in FIGS. 8 and 10. To prepare a maxillary denture from individual artificial teeth, the practitioner first obtains, using the labial drape locator 30, and methodology heretofore described, a measurement of the patient's incisal length and labial drape. The labial drape locator 30 is fully inserted within opening 22 and the location of the maxillary base member and position of the maxillary cast within flask 6 adjusted, as previously described, until the palatine papilla of the cast contacts the upper terminal portion of pin 31. Set screw 15 is closed fixing the height of the maxillary base relative to the occlusal base member. The maxillary base member is then pivoted away from the occlusal base member (as in FIG. 1), pin 31 removed from labial drape locator 30 which in turn is positioned within opening 22. The configuration of the arch locator 40 actually used is dependent upon the anatomy of the patient. Typically, the arch locator conforms to a standard maxillary or mandibular arch index, as applicable, that conforms most closely to the patients actual arch size.

Putty is placed within the slot (arch form) defined by the two elements of the arch locator 40. The individual teeth are then set in the putty firmly against the occlusal base member and against the outer periphery of the arch form (see FIG. 8). The individual artificial teeth are adhered to the maxillary cast by placing a sufficient quantity of wax on top of the artifical teeth positioned by the arch locator and lowering the maxillary cast onto the wax until the maxillary base member 4 is parallel to the upper surface 21 of the occlusal base member 20. The resulting "wax-up" can then be processed, as described hereafter, or used to prepare the complementing mandibular denture.

To prepare the mandibular denture, using individual artifical teeth, the maxillary wax-up is removed from the cast and placed in the patient's mouth. Using the maxillary wax-up the patient bites upon a wax bite block that is positioned over the patient's mandibular arch. The maxillary wax-up is then replaced onto the cast contained in flask 6 and the bite block (trimmed) brought in congruence with the same and held in place thereon with rubber bands (see FIG. 9). The mandibular cast positioning means 7 is removed from the mandibular base member 1 (held in place by screws passing through the underside of mandibular base member 1), placed within lower flask 6 and refixed to base member 1. In a preferred embodiment the cast positioning means forms the bottom of flask 6. The lower flask 6 is then partially filled with plaster and the maxillary wax-up/bite block structure lowered into the plaster until the maxillary base member 4 is parallel to the upper surface of the mandibular base member 1 (See FIG. 9).

After the plaster has cured, the maxillary cast and flask 6 should be removed from the maxillary base member 4 and the mandibular cast and flask placed upon maxillary base member 4. The occlusal base member 20 should be put back into position on the relator assembly and the labial drape locator 30 (adjusted as previously described) inserted within opening 22. The mandibular shim 42 should be positioned on the labial drape locator 30 and the appropriately sized arch locator 40 placed upon the upper surface of mandibular shim 42. Mandibular shim 42 is held in position by studs 35 and 37 of the labial drape locator 30. Studs corresponding to studs 35 and 37 are formed on the upper surface of shim 42 and serve to locate and position the elements of arch locator 40. The mandibular shim 42 is about 10–20 millimeters thick and is used to compensate for the protrusion of the heels area of the mandibular cast (retromolar pad area) through the plane of occlusion (see FIG. 11).

Putty is then placed in the slot defined by the two components of the arch locator 40. Artifical mandibular teeth are placed in the putty at proper locations and angulations. Wax is placed on top of the tooth structure. The vertical distance between the maxillary base member 4 and the upper surface of the occlusal base member 20 that was set when the maxillary wax-up was prepared is now increased by an amount equal to the thickness of the mandibular shim 42. This is accomplished by releasing set screw 15 and rotating adjusting screw 14 until the additional required distance is achieved. Pointer 16, located at the end of crossbar 11, and scale 17, located on post 13, can be used to ascertain the amount of vertical distance alterations. Thereafter, the mandibular cast (after removal of the bite block) is lowered onto the wax to form a mandibular wax-up (see FIG. 11).

To secure a completed maxillary denture the cast/impression material 51/prefabricated arch structure "sandwich" described earlier is processed further using techniques well known to those skilled in the art. In a preferred method, the maxillary "sandwich" is placed within a segment of a flask system and covered with an additional impression material in amount sufficient to fill the flask. In a preferred embodiment, cast positioning means 7 functions as the bottom element of the flask system. Thereafter, the lid of the flask system and sprues are put in place and the entire assembly clamped together. After the impression material has solidified, the flask is opened and the resulting system separated into its component parts, namely, a new impression of the arch structure "sandwich," the prefabricated arch element, the piece of solidified impression material 51 that was formed between the prefabricated arch structure and the cast during use of the relator and, finally, the original cast element. Thereafter, the flask structure is reassembled leaving from the system the impression material 51 that was obtained with the use of the relator assembly. A void left by the removal of impression material 51 is filled with an appropriate liquid thermosetting or thermoplastic resin material, the flask sealed and the total flask system heated at elevated temperature and pressure for a time sufficient to cure the resin material within the flask system and integrally bond the same to the prefabricated denture structure. After trimming, the finished maxillary denture which is related to Camper's Plane can be fitted to the patient.

The maxillary and mandibular wax-ups can be processed in the same manner except that the flask is placed in boiling water after solidification of the new impression material to melt and remove the wax. The void left by the melted wax is filled with resinous material and cured as described above.

What is claimed is:

1. A relator assembly useful for preparing dentures or denture elements that are anatomically related to Camper's Plane comprising:
    (a) a stand member;
    (b) a vertically disposed support means having an upper and lower portion, said lower portion connected to said stand member;
    (c) a horizontally disposed occlusal base member having an upper surface and adapted to be located above said stand member;
    (d) a maxillary base member, having an upper and lower surface, pivotably connected to the upper portion of said support means, the lower surface of said maxillary base member adapted to be positioned in substantial vertical alignment with and in a plane parallel to the upper surface of said occlusal base member;
    (e) cast positioning means located on the lower surface of said maxillary base member;
    (f) a labial drape locator adapted to be positioned on and removed from the upper surface of the occlusal base member and comprising (i) a removable pin member, (ii) an elongated pin holder, having an inner end and an outer end, adapted to locate and position said pin member adjacent the inner end thereof in a plane substantially perpendicular to the upper surface of said occlusal base member and (iii) an arch locator holder interconnected to said pin holder and horizontally adjustable relative to the inner end of said pin holder; and (g) an arch locator adapted to be positioned on and removed from said arch locator holder, said arch locator functioning to locate a prefabricated denture or denture element on the said occlusal base member.

2. The apparatus of claim 1 wherein the upper portion of said support means is vertically movable in relation to the lower portion of said support means.

3. A relator assembly useful for preparing dentures or denture elements that are anatomically related to Camper's Plane comprising:

(a) a horizontally disposed mandibular base member having an upper surface;

(b) a vertically disposed support means having an upper and lower portion, said lower portion connected to said mandibular base member and the upper portion of said support means being vertically movable in relation to the lower portion of said support member;

(c) a horizontally disposed occlusal base member having an upper surface and adapted to be located above the said mandibular base member;

(d) a maxillary base member having an upper and lower surface pivotably connected to the upper portion of said support means, the lower surface of said maxillary base member adapted to be positioned in substantial alignment with and in a plane parallel to the upper surface of said occlusal base member;

(e) cast positioning means located on the lower surface of the maxillary base member and on the upper surface of the mandibular base member, said cast positioning means being in substantial vertical alignment with each other;

(f) a labial drape locator adapted to be positioned on and removed from the upper surface of the occlusal base member and comprising (i) a removable pin member, (ii) an elongated pin holder, having an inner end and an outer end, adapted to locate and position said pin member adjacent the inner end thereof in a plane substantially perpendicular to the upper surface of said occlusal base member and (iii) an arch locator holder interconnected to said pin holder and horizontally adjustable relative to the inner end of said pin holder; and (g) an arch locator adapted to be positioned on and removed from the said arch locator holder, said arch locator functioning to locate a prefabricated denture or denture element on said occlusal base member.

4. The apparatus of claim 3 wherein said occlusal base member is removably connected to the upper surface of the mandibular base member.

* * * * *